United States Patent [19]

Hardtmann

[11] 3,959,279

[45] *May 25, 1976

[54] 1-SUBSTITUTED-2-IMINO-QUINAZOLIN-4(1H)ONES

[75] Inventor: Goetz E. Hardtmann, Florham Park, N.J.

[73] Assignee: Sandoz, Inc., E. Hanover, N.J.

[ * ] Notice: The portion of the term of this patent subsequent to Feb. 3, 1993, has been disclaimed.

[22] Filed: July 24, 1974

[21] Appl. No.: 491,214

Related U.S. Application Data

[63] Continuation-in-part of Ser. No. 437,469, Jan. 28, 1974, abandoned, which is a continuation-in-part of Ser. No. 373,476, June 25, 1973, abandoned, which is a continuation-in-part of Ser. No. 339,370, March 8, 1973, abandoned.

[52] U.S. Cl.............. 260/256.4 Q; 260/244 A; 260/552 R; 424/251
[51] Int. Cl.².................................. C07D 239/95
[58] Field of Search............................ 260/256.4 Q

[56] References Cited
UNITED STATES PATENTS 3,149,106  9/1964  Loev........................ 260/256.4 Q
3,168,521  2/1965  Wagner..................... 260/256.4 Q
3,558,610  1/1971  Breuer et al................ 260/256.4 Q FOREIGN PATENTS OR APPLICATIONS
105,765  11/1966  Denmark.................... 260/256.4 Q

*Primary Examiner*—Alton D. Rollins
*Assistant Examiner*—David E. Wheeler
*Attorney, Agent, or Firm*—Gerald D. Sharkin; Richard E. Vila

[57] ABSTRACT

Anti-Histaminics of the formula

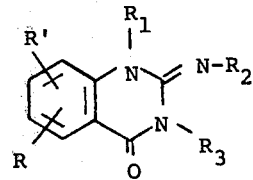

wherein $R_1$ is alkyl, alkenyl or phenalkyl, $R_2$ and $R_3$ are hydrogen, alkyl or alkenyl and R and R' are optional are prepared by reacting a 1-substituted isatoic anhydride with a S-methyl-thiopseudourea.

22 Claims, No Drawings

1-SUBSTITUTED-2-IMINO-QUINAZOLIN-4(1H)ONES

This application is a continuation-in-part of now abandoned application Ser. No. 437,469, filed Jan. 28, 1974, which in turn is a continuation-in-part of now abandoned application Ser. No. 373,476, filed June 25, 1973, which in turn is a continuation-in-part of now abandoned application Ser. No. 339,370, filed Mar. 8, 1973.

This invention relates to 1,2-disubstituted-quinazolin-4(1H)-ones, their preparation and the compositions and methods utilizing the pharmacological activity of said compounds.

The compounds of the invention may be represented by the structured formula I:

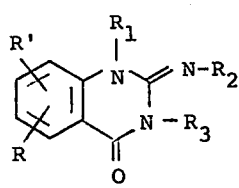
I wherein
$R_1$ is alkyl of 1 to 6 carbon atoms, alkenyl of 3 to 8 carbon atoms or phenalkyl of the formula II:

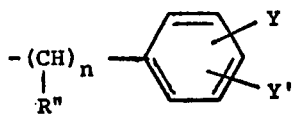
II $n$ is 1 or 2

$R''$ is hydrogen or methyl provided that $R''$ is hydrogen when n is 2, $R_2$ is hydrogen, alkyl of 1 to 6 carbon atoms or alkenyl of 3 to 6 carbon atoms, $R_3$ is hydrogen, alkyl of 1 to 6 carbon atoms or alkenyl of 3 to 6 carbon atoms, R and R' are independently hydrogen, halo of atomic weight of from 18 to 36, alkyl of 1 to 3 carbon atoms or alkoxy of 1 to 3 carbons or one is hydrogen and the other bromo or trifluoromethyl, and Y and Y'' are independently hydrogen, halo of atomic weight of from 18 to 36, alkyl of 1 to 3 carbon atoms or alkoxy of 1 to 3 carbon atoms or one is hydrogen and the other bromo or trifluoromethyl.

The compounds of the formula I may be prepared in a Step A by reacting a compound of the formula III:

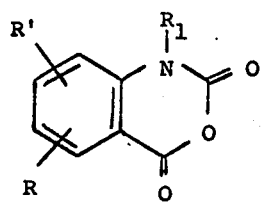
III wherein $R_1$, R and R' are as above defined, with a compound of the formula IV:

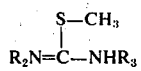

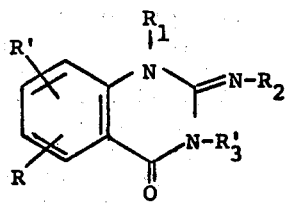
IV wherein $R_2$ and $R_3$ are as above defined.

The compounds of the formula I having the formula Ia:

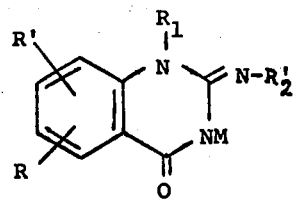
Ia in which R, R', $R_1$ and $R_2$ are as above defined and $R_3'$ is alkyl of 1 to 6 carbon atoms or alkenyl of 3 to 6 carbon atoms, may also be prepared in a Step B reaction by reacting a compound of the formula Ib:

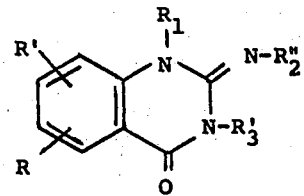
Ib in which R, R' and $R_1$ are as defined, M is hydrogen or an alkali metal, preferably sodium and $R_2'$ is hydrogen, alkyl of 1 to 6 carbon atoms, alkenyl or 3 to 6 carbon atoms or M as above defined, with an alkylating or alkenylating agent of the formula V:

$$X-R_3' \qquad V$$

in which $R_3'$ is as above defined and X is halo of atomic weight of from 35 to 127, preferably iodo or bromo.

The compounds of the formula I having the formula Ic:

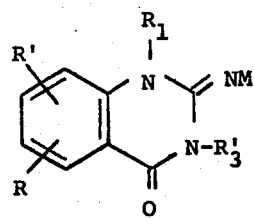
Ic in which R, R', $R_1$ and $R_3'$ are as defined and $R_2''$ is alkyl of 1 to 6 carbon atoms or alkenyl of 3 to 6 carbon atoms, may also be prepared in a Step C reaction by reacting a compound of the formula Id:

Id in which M, R, R', $R_1$ and $R_3'$ are as defined, with an alkylating or alkenylating agent of the formula VI:

   VI in which X and $R_2''$ are as defined.

The preparation of compounds I by the reaction of Step A can be carried out at temperatures in the range of 20°C. to 200°C., more usually 80°C. to 180°C., preferably 100°C. to 180°C. The reaction is conveniently carried out in an organic solvent of conventional type providing an inert reaction medium. The higher boiling solvents for use at reflux temperatures represent the preferred solvents, e.g., toluene, xylene and especially diglyme and the like. The reaction is preferably carried out in the presence of a base, e.g., potassium hydroxide, sodium hydroxide, barium hydroxide and potassium carbonate; and when the compound IV is employed directly in acid addition salt form, it is of course desirable to employ an amount of base greater than the amount necessary to neutralize the acid. It will be appreciated by those skilled in the art that the compounds of the formula IV are tautomeric and have the alternative and equivalent structure represented by the formula IVA:

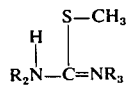   IVA wherein $R_2$ and $R_3$ are as above defined. It thus may be foreseen that the reaction of Step A in which $R_2$ and $R_3$ in the compounds IV (and IVA) are dissimilar may lead to mixtures of the final products of the formula I in which $R_2$ has the meaning of $R_2$ in one of the products and $R_3$ in the other product and, correspondingly, $R_3$ will have the meaning of $R_3$ in one of the products and the meaning of $R_2$ in the other product. When $R_2$ is alkyl or alkenyl and $R_3$ is hydrogen in the compound IV it has been observed that the clear direction of the reaction is to form the final products in which $R_2$ is alkyl or alkenyl and $R_3$ is hydrogen. Accordingly, the final products of the formula I in which $R_2$ is hydrogen and $R_3$ is alkyl or alkenyl are in general preferably prepared by reaction Step B. Similarly, the final products in which $R_2$ and $R_3$ are dissimilar alkyl and/or alkenyl groups may in some instances also be preferably prepared by the reaction of Step B and Step C. In general, the reaction product of formula I may be recovered from the reaction of Step A by working up by conventional procedures.

The reaction of Step B is of known type and preferably effected employing a compound Ib in which M is an alkali metal. Such compounds Ib may be prepared from the corresponding compound Ib in which M is hydrogen in a known manner involving the reaction of a compound Ib in which M is hydrogen with a strong base such as an alkali metal hydride or alkoxide, preferably sodium hydride. The reaction is conveniently effected at from 0°C. to 50°C., preferably at about room temperature, in an inert solvent which can be employed as solvent for the reaction of Step B. The conversion of the metallo substituted quinazolinone of the formula Ib to the desired product may be carried out at temperatures of from 0°C. to 100°C., preferably 10°C. to 40°C. and conveniently at room temperature. When the Step B reaction is carried out with a compound Ib in which M is hydrogen, the reaction is conducted in the presence of the strong base, e.g. sodium hydride. In either case, the conditions of time, temperature and quantity of strong base and compound V are generally controlled based on the observation that the alkylation or alkenylation procedure of Step B favors the 3- position of the compound of the formula Ib. For example, when employing a compound of the formula Ib in which $R_2'$ is hydrogen, the more controlled or limited conditions favor the production of the compound of the formula Ia in which $R_2$ is hydrogen. On the other hand, increased quantities of the strong base and alkylating or alkenylating agent and the longer reaction times and higher temperatures will result in increased quantities of the compound of the formula Ia in which $R_2$ and $R_3'$ are similar alkyl or alkenyl groups. Since the compounds of the formula I in which $R_2$ and $R_3$ are similar alkyl or alkenyl groups are very conveniently prepared by the Step A reaction, it will be evident that the reaction of Step B should merit serious consideration only when producing final products in which $R_2$ and $R_3$ are dissimilar.

The reaction of Step C and the preparation of the intermediates of the formula Id in which M is an alkali metal from a compound Id in which M is hydrogen are carried out analogously to the reaction of Step B. It will be further evident that Step C will also only merit serious consideration when producing compounds of the formula Ic in which $R_2''$ and $R_3'$ are dissimilar alkyl and/or alkenyl groups.

The compounds of the formulae III, IV, V and VI are either known or may be produced from known materials by established procedures.

The compounds of the formula I in which both $R_2$ and $R_3$ are hydrogen form acid addition salts and the pharmaceutically acceptable acid addition salts not materially depreciating the pharmacological effect of said compounds are included within the scope of the compounds of the formula I of the invention. Such salts include the well known pharmaceutically acceptable salts, e.g. the hydrochloric, maleate, etc. The acid addition salts may be produced from the corresponding free base by conventional procedures. Conversely, the free bases may be obtained from the salts by procedures known in the art.

The compounds of formula I of the invention are useful because they possess biological activity. In particular, the compounds of the formula I are useful as agents for relieving the symptomatic effects of the release of histamine, i.e. as anti-histaminic agents, as indicated by observing the respiratory status on oral administration (0.1–100 mgs/kgs) to the unanesthetized guinea pig exposed to aerosolized histamine dihydrochloride according to a modification of the method of Van Arman et al. J. Pharmacol. Exptl. Therap. 113: 90–97, 1961. For such use and depending upon known variables satisfactory results are obtained in general on the daily administration of from 0.1 to 100 milligrams per kilogram of body weight, preferably given in divided doses to 2 to 4 times a day, or in sustained release form. For most mammals the administration of from 8 to 1600 milligrams per day provides satisfactory results and dosage forms suitable for internal administration comprise 2 to 800 milligrams of the compound in admixture with a solid or liquid pharmaceutical carrier or diluent.

The preferred compounds of the invention from the standpoint of anti-histaminic activity are those in which $R_1$ is benzyl including substituted benzyl, particularly unsubstituted benzyl and halobenzyl, e.g. fluorobenzyl, especially 4-halobenzyl, and the more preferred compounds are those in which each of R and R' is hydrogen. Special mention may be made, for example, of the compound 1-(4'-fluorobenzyl(-2-methylamino-quinazolin-4(1H)-one in view of its surprisingly potent response in the aerosolized histamine test.

For the use indicated above, the compounds may be combined with a pharmaceutically acceptable carrier, and such other conventional adjuvants as may be necessary, and administered orally or parenterally. For most uses oral administration with carriers is preferred and may take place in such conventional forms as tablets, dispersible powders, granules, capsules, suspensions, syrups and elixirs. Such compositions may be prepared according to any method known in the art for the manufacture of pharmaceutical compositions, and such compositions may contain one or more conventional adjuvants, such as sweetening agents, flavoring agents, coloring agents and preserving agents, in order to provide an elegant and palatable preparation. Tablets may contain the active ingredient in admixture with conventional pharmaceutical excipients, e.g., inert diluents such as calcium carbonate, sodium carbonate, lactose and talc, granulating and disintegrating agents, e.g., starch and alginic acid, binding agents, e.g., starch, gelatin and acacia, and lubricating agents, e.g., magnesium stearate, stearic acid and talc. The tablets may be uncoated or coated by known techniques to delay disintegration and adsorption in the gastrointestinal tract and thereby provide a sustained action over a longer period. Similarly, suspensions, syrups and elixirs may contain the active ingredient in admixture with any of the conventional excipients utilized for the preparation of such compositions, e.g., suspending agents (methylcellulose, tragacanth and sodium alginate), wetting agents (lecithin, polyoxyethylene stearate and polyoxyethylene sorbitan monooleate) and preservatives (ethyl-p-hydroxybenzoate). Capsules may contain the active ingredient alone or admixed with an inert solid diluent, e.g., calcium carbonate, calcium phosphate and kaolin. The preferred pharmaceutical compositions from the standpoint of preparation and ease of oral administration are solid compositions, particularly hard-filled capsules and tablets. Parenteral administration may be in such conventional forms as injectionable solutions and suspensions.

A representative formulation is a tablet for oral administration two to four times a day for relieving the effects of histamine release and prepared by conventional tabletting techniques to contain the following ingredients:

| Ingredients | Weight (mg.) |
|---|---|
| 1-(4'-fluorobenzyl)-2-methyl-amino-quinazolin-4(1H)-one | 20 |
| Tragacanth | 10 |
| Lactose | 222.5 |
| Corn Starch | 25 |
| Talcum | 15 |
| Magnesium Stearate | 2.5 |

It will be evident to those skilled in the art that the compounds of the formula I in which $R_3$ is hydrogen are tautomeric and have the alternative and equivalent structure represented by the formula IA:

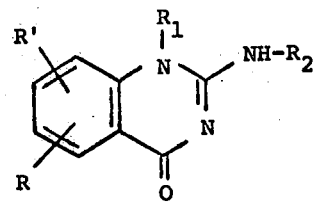

IA wherein R, R' and $R_1$ are as defined.

The following examples show representative compounds encompassed within the scope of this invention and the manner in which such compounds are prepared. However, it is to be understood that the examples are for purposes of illustration only.

EXAMPLE 1

1-(4'-fluorobenzyl)-2-amino-quinazolin-4(1H)-one.

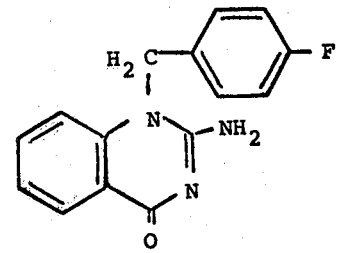

A mixture of 20 g. of N-(p-fluorobenzyl)isatoic anhydride, 15 g. of S-methylthiopseudourea (hydrogen sulfate), 17.5 g. of barium hydroxide and 250 ml. of toluene is refluxed with stirring for 18 hours. The resulting mixture is evaporated to dryness, the residue suspended in 500 ml. of hot methanol, filtered and treated with maleic acid in methanol. After partial evaporation on a steam bath the resulting precipitate is recovered by filtering, washed with ether and dried under reduced pressure to obtain the titled product in maleate salt form, m.p. 217°–221°C. The product is suspended in 700 ml. of water, treated with 100 ml. 1N sodium hydroxide solution, warmed for one hour, cooled, filtered off insoluble material and dissolved this in hydrochloric acid, precipitated the base with sodium carbonate, washed it well with water and dried at 50°C. under reduced pressure to obtain the titled product (free base form), m.p. 170°C.

EXAMPLE 2

Following the procedure of Example 1, the following additional compounds of the invention are prepared.

A) 1-benzyl-2-amino-quinazolin-4(1H)-one.
B) 1-(3,4'-dimethoxybenzyl)-2-amino-quinazolin-4(1H)-one.
C) 1-(3'-trifluoromethylbenzyl)-2-amino-quinazolin-4(1H)-one.
D) 1-(4'-bromobenzyl)-2-amino-quinazolin-4(1H)-one.
E) 7-chloro-1-(4'-fluorobenzyl)-2-amino-quinazolin-4(1H)-one.
F) 6,7-dimethoxy-1-(4'-fluorobenzyl)-2-aminoquinazolin-4(1H)-one.

G) 2,3-dihydro-1-(4'-fluorobenzyl)-3-methyl-2-methylimino-quinazolin-4(1H)-one, m.p. 71°–73°C.

H) 1-(4'-fluorobenzyl)-2-methylamino-quinazolin-4(1H)-one, m.p. 253°–256°C.

I) 1-(4'-fluorobenzyl)-2-ethylamino-quinazolin-4(1H)-one, m.p. 218°–220°C.

J) 1-benzyl-2-methylamino-quinazolin-4(1H)-one, m.p. 292°–295°C.

K) 1-ethyl-2-methylamino-quinazolin-4(1H)-one, m.p. 262°–264°C.

L) 1-(4'-fluorobenzyl)-2-butylamino-quinazolin-4(1H)-one.

M) 1-(5-hexenyl)-2-methylamino-quinazolin-4(1H)-one.

N) 1-(2-butenyl)-2-methylamino-quinazolin-4(1H)-one.

O) 1-allyl-2-methylamino-quinazolin-4(1H)-one, m.p. 202°–204°C.

EXAMPLE 3

1-(4'-fluorobenzyl)-2-imino-3-methyl-2,3-dihydroquinazolin-4(1H)-one.

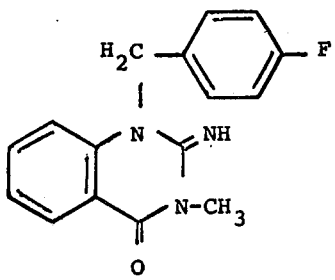

To a mixture of 570 mg. of sodium hydride in 50.0 ml. of dimethylacetamide is added 2.7 g. of 1-(4'-fluorobenzyl)-2-amino-quinazolin-4(1H)-one followed by stirring for one hour at room temperature. There is then added 3.0 g. of methyl iodide and the resulting solution is stirred for 18 hours at room temperature. The resulting mixture is then evaporated in vacuo to remove the solvent and the residue stripped twice with benzene. The resulting residue is poured over ice-water and the precipitate which forms (about 0.5 hour) is washed with water, dried by suction, dissolved in methylene chloride, treated with sodium sulfate, alumina and charcoal and then filtered through Celite. The solvent is exchanged for ether and concentration results in a precipitate which is recovered by filtering, washed with pentane and dried under reduced pressure to obtain 1-(4'-fluorobenzyl)-2-imino-3-methyl-2,3-dihydro-quinazolin-4(1H)-one, m.p. 135°–137°C.

EXAMPLE 4

Following the procedure of Example 3, the following additional compounds of the invention are prepared:

A) 1-(4'-fluorobenzyl)-2-imino-3-allyl-2,3-dihydroquinazolin-4(1H)-one.

EXAMPLE 5

1-(4'-fluorobenzyl)-2-allylamino-quinazolin-4(1H)-one.

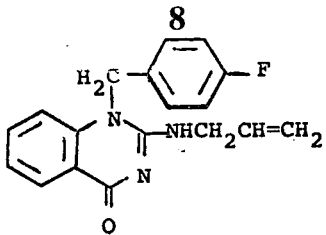

A suspension of 13.5 g. of N-(4'-fluorobenzyl)isatoic anhydride, 130 g. of S-methyl-N-allylthiopseudourea hydroiodide and 75 g. of powdered sodium carbonate in 500 ml. of acetonitrile is heated with stirring at reflux for 1.5 hours. The excess sodium carbonate is filtered off and the solvent evaporated to dryness. The residue is dissolved in methylene chloride, filtered to remove insolubles and the filtrate evaporated to dryness. The residue is dissolved in 500 ml. of diglyme and the resulting solution heated at reflux for 1.5 hours. After cooling, methylene chloride is added to obtain a precipitate which is recovered by filtering, washed twice with methylene chloride and once with ether, dried, dissolved in methanol, filtered and concentrated on a steam bath to obtain a precipitate which is recovered by filtering, washed with methanol and dried under reduced pressure to obtain 1-(4'-fluorobenzyl)-2-allylamino-quinazolin-4(1H)-one, m.p. 155°–157°C. (additional quantities of the title compound are recovered from the mother liquid).

EXAMPLE 6

1-(4'-fluorobenzyl)-2-methylamino-quinazolin-4(1H)-one

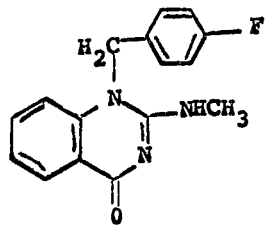

A mixture of 15 g. of N-(p-fluorobenzyl)isatoic anhydride, 15 g. of N,S-dimethylthiopseudourea (hydrogen iodide), 9.0 g. of potassium carbonate and 250 ml. of diglyme is refluxed with stirring for 1.5 hours. The resulting mixture is filtered while hot, cooled and the resulting precipitate is recovered by filtering, dissolved in methanol, dried, treated with charcoal, filtered through celite, concentrated on a steam bath and cooled to obtain a precipitate which is recovered by filtering, washed with ether and dried under reduced pressure to obtain 1-(4'-fluorobenzyl)-2-methylamino-quinazolin-2(1H)-one, m.p. 251°–255°C.

The compounds of the formula Ie:

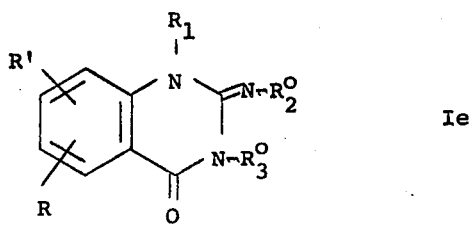

Ie wherein R, R' and $R_1$ are as above defined and $R_2^o$ and $R_3^o$ are respectively the same as $R_2$ and $R_3$ as above defined but subject to the provision that $R_2^o$ is a hydrocarbon when $R_3^o$ is a hydrocarbon, may also be prepared in a Step D reaction involving cyclizing a compound of the formula VII:

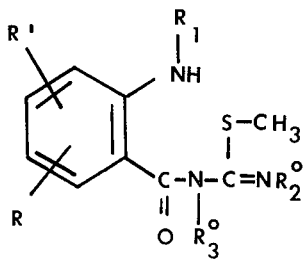

VII wherein R, R', $R_1$, $R_2^o$ and $R_3^o$ are as defined.

The preparation of compounds of the formula Ie by the reaction of Step D may be carried out by heating a compound of the formula VII at elevated temperatures in the range of 60°C. to 200°C., more preferably 90°C. to 150°C., and desirably in the presence of an inert solvent and strong base. The inert solvents may be of conventional type, e.g., dioxane and diglyme. Suitable strong bases include the strong inorganic bases such as the alkali metal hydroxides, e.g., sodium hydroxide. Reaction time may vary, particularly with temperature, with good results usually obtained in one-half to ten hours.

The compounds of the formula VII employed in Step D may be prepared by reacting a compound of the formula III with a compound of the formula IV under controlled temperature and time conditions. In general, temperatures are usually in the range of from 20°C. to 110°C., preferably 60°C. to 105°C. Reaction times may be typically of the order of from 10 minutes to 5 hours and generally will vary inversely with reaction temperature. The reaction is preferably carried out in the presence of a base such as an inorganic base, e.g., potassium carbonate or sodium carbonate, and in the presence of an inert solvent of conventional type. The solvents boiling at reflux temperatures are generally preferred, e.g., acetonitrile and benzene. The resulting product of the formula VII may, if desired, be isolated and recovered by working up by conventional procedures.

It will be evident that the compounds of the formula VII in which $R_3^o$ is hydrogen exist in and be expressed by the alternative and equivalent tautomeric form having the formula VIIA:

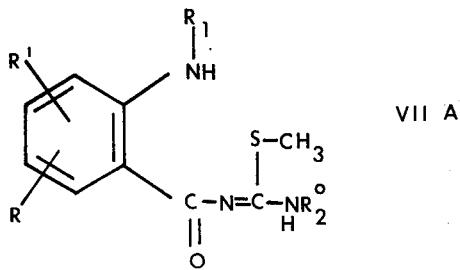

VII A in which R, R', $R_1$ and $R_2^o$ are as defined.

EXAMPLE 7

1-ethyl-2-methylamino-quinazolin-4(1H)-one (alternate procedure)

Step A: Preparation of S,3-dimethyl-1-(N-ethylanthranoyl)thiourea

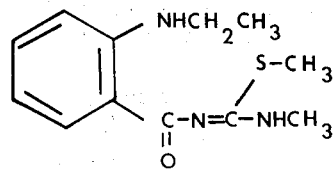

A mixture of 9.6 g. of N-ethylisatoic anhydride, 12 g. of N,S-dimethylthiopseudourea(hydrogen iodide), 7 g. of sodium carbonate and 150 ml. of acetonitrile is refluxed for 2 hours, filtered while hot and evaporated to dryness. The residue is dissolved in methylene chloride, filtered, the filtered material washed with methylene chloride and the combined methylene chloride liquors concentrated in vacuo. The concentrated solution is treated by addition of methanol, cooled and the resulting precipitate recovered by filtering, washed with methanol and dried under reduced pressure at 60°C. to obtain S,3-dimethyl-1-(N-ethylanthranoyl)thiourea, m.p. 54°-57°C.

Step B: Preparation of 1-ethyl-2-methylamino-quinazolin-4(1H)-one.

A mixture of 6.5 g. of S,3-dimethyl-1-(N-ethylanthranoyl)-thiourea, 1 pellet of sodium hydroxide and 100 ml. of dioxane is heated on a steam bath for 5 hours. The resulting mixture is cooled and the resulting precipitate is recovered by filtering, washed with ether, dissolved in methanol, dried, treated with charcoal, filtered through celite and the methanol exchanged for chloroform. Ether is then added and the resulting precipitate recovered by filtering, washed with ether, dried under reduced pressure, dissolved in chloroform, treated with sodium carbonate and then charcoal, dried, filtered through celite and the chloroform exchanged for methylene chloride. Evaporation in vacuo results in a precipitate which is recovered by filtering, washed with cold methylene chloride and dried under reduced pressure to obtain 1-ethyl-2-methylamino-quinazolin-4(1H)-one, m.p. 262°-264°C.

EXAMPLE 8

Following the procedure of Step A of Example 7, the following compounds are prepared:

A) S,3-dimethyl-1-[N-(4'-fluorobenzyl)anthranoyl] thiourea.
B) S-methyl-3-allyl-1-[N-(4'-fluorobenzyl)anthranoyl] thiourea.

What is claimed is:
1. A compound of the formula

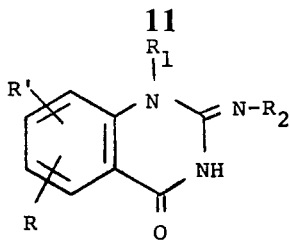

wherein
R₁ is alkyl of 1 to 6 carbon atoms, alkenyl of 3 to 8 carbon atoms or phenalkyl of the formula:

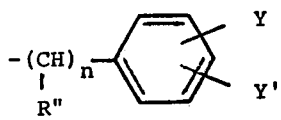

n is 1 or 2
R'' is hydrogen or methyl provided that R'' is hydrogen when n is 2,
R₂ is hydrogen, alkyl of 1 to 6 carbon atoms or alkenyl of 3 to 6 carbon atoms,
R and R' are independently hydrogen, fluoro, chloro, alkyl of 1 to 3 carbon atoms or alkoxy of 1 to 3 carbons or one is hydrogen and the other bromo or trifluoromethyl, and
Y and Y' are independently hydrogen, fluoro, chloro, alkyl of 1 to 3 carbon atoms or alkoxy of 1 to 3 carbon atoms or one is hydrogen and the other bromo or trifluoromethyl, or a pharmaceutically acceptable acid addition salt of the compounds in which R₂ is hydrogen.

2. A compound of claim 1 in which R₂ is hydrogen.
3. A compound of claim 1 in which R₂ is alkyl.
4. A compound of claim 3 in which R₂ is alkyl of 1 to 3 carbon atoms.
5. A compound of the formula:

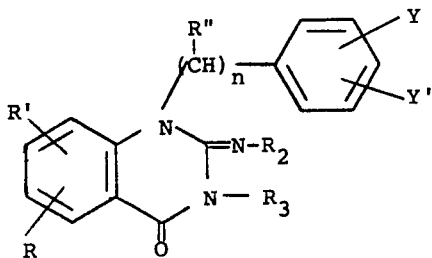

wherein
n is 1 or 2,
R'' is hydrogen or methyl provided that R'' is hydrogen when n is 2,
R₂ is hydrogen, alkyl of 1 to 6 carbon atoms or alkenyl of 3 to 6 carbon atoms,
R₃ is hydrogen, alkyl of 1 to 6 carbon atoms or alkenyl of 3 to 6 carbon atoms,
R and R' are independently hydrogen, fluoro, chloro, alkyl of 1 to 3 carbon atoms or alkoxy of 1 to 3 carbon atoms or one is hydrogen and the other bromo or trifluoromethyl, and
Y and Y' are independently hydrogen, fluoro, chloro, alkyl of 1 to 3 carbon atoms or alkoxy of 1 to 3 carbon atoms or one is hydrogen and the other bromo or trifluoromethyl, or
a pharmaceutically acceptable acid addition salt of the compounds in which each of R₂ and R₃ is hydrogen.

6. A compound of claim 5 in which R'' is hydrogen, n is 1 and Y and Y' are selected from the group consisting of hydrogen, fluoro, chloro and bromo.
7. A compound of claim 6 in which Y is 4-fluoro, 4-chloro or 4-bromo and Y' is hydrogen.
8. A compound of claim 6 in which Y and Y' are hydrogen.
9. A compound of claim 6 in which R and R' are hydrogen.
10. A compound of claim 6 in which R₂ is hydrogen or alkyl and R₃ is hydrogen.
11. A compound of claim 9 in which R₂ is hydrogen or alkyl and R₃ is hydrogen.
12. A compound of claim 11 in which R₂ is alkyl.
13. A compound of claim 12 in which R₂ is alkyl of 1 to 3 carbon atoms.
14. A compound of claim 6 in which each of R₂ and R₃ is alkyl.
15. A compound of claim 14 in which R₂ and R₃ are the same.
16. The compound of claim 15 which is 2,3-dihydro-1-(4'-fluorobenzyl)-3-methyl-2-methylimino-quinazolin-4(1H)-one.
17. The compound of claim 9 which is 1-(4'-fluorobenzyl)-2-amino-quinazolin-4(1H)-one.
18. The compound of claim 13 which is 1-(4'-fluorobenzyl)-2-methylamino-quinazolin-4(1H)-one.
19. The compound of claim 13 which is 1-(4'-fluorobenzyl)-2-ethylamino-quinazolin-4(1H)-one.
20. The compound of claim 13 which is 1-benzyl-2-methylamino-quinazolin-4(1H)-one.
21. A compound of claim 1 in which R₂ is alkenyl.
22. The compound of claim 21 which is 1-(4'-fluorobenzyl)-2-allylamino-quinazolin-4(1H)-one.

* * * * *